United States Patent
Cull

(10) Patent No.: US 9,821,108 B2
(45) Date of Patent: Nov. 21, 2017

(54) ARTERIOVENOUS ACCESS VALVE SYSTEM AND PROCESS

(71) Applicant: DIAXMED, LLC, Raleigh, NC (US)

(72) Inventor: David L. Cull, Greenville, SC (US)

(73) Assignee: DIAXAMED, LLC, Raleigh, NC (US)

( * ) Notice: Subject to any disclaimer, the term of this patent is extended or adjusted under 35 U.S.C. 154(b) by 747 days.

(21) Appl. No.: 14/340,763

(22) Filed: Jul. 25, 2014

(65) Prior Publication Data

US 2014/0336558 A1    Nov. 13, 2014

Related U.S. Application Data

(63) Continuation of application No. 13/442,448, filed on Apr. 9, 2012, now Pat. No. 8,790,288, and a continuation of application No. 11/807,479, filed on May 29, 2007, now abandoned.

(51) Int. Cl.
| | |
|---|---|
| *A61M 39/02* | (2006.01) |
| *A61M 39/22* | (2006.01) |
| *A61M 1/36* | (2006.01) |
| *A61F 2/06* | (2013.01) |
| *A61F 2/24* | (2006.01) |

(52) U.S. Cl.
CPC .......... *A61M 1/3655* (2013.01); *A61F 2/06* (2013.01); *A61M 39/227* (2013.01); *A61M 39/228* (2013.01); *A61F 2/2475* (2013.01); *A61M 39/0208* (2013.01); *A61M 2205/04* (2013.01)

(58) Field of Classification Search
CPC .............. A61M 1/3655; A61M 39/227; A61M 39/228; A61M 39/0208; A61M 2205/04; A61F 2/06; A61F 2/2475
USPC .................................................... 604/4.01–10
See application file for complete search history.

(56) References Cited

U.S. PATENT DOCUMENTS

| | | | |
|---|---|---|---|
| 4,828,544 A * | 5/1989 | Lane ...................... | A61B 17/12 128/DIG 25 |
| 5,713,859 A | 2/1998 | Finch, Jr. et al. | |
| 6,090,067 A | 7/2000 | Carter | |
| 6,319,465 B1 | 11/2001 | Schnell et al. | |
| 7,025,741 B2 | 4/2006 | Cull | |
| 7,144,381 B2 | 12/2006 | Gertner | |
| 7,223,257 B2 | 5/2007 | Shubayev et al. | |

(Continued)

OTHER PUBLICATIONS

Patent Cooperative Treaty International Search Report, dated Jan. 29, 2010. (4 pages).

(Continued)

*Primary Examiner* — Susan Su
(74) *Attorney, Agent, or Firm* — Dority & Manning, P.A.

(57) ABSTRACT

An arteriovenous graft system is described. The arteriovenous graft system includes an arteriovenous graft that is well suited for use during hemodialysis. In order to minimize or prevent arterial steal, at least one valve device is positioned at the arterial end of the arteriovenous graft. In one embodiment, for instance, the arteriovenous graft system includes a first valve device positioned at the arterial end and a second valve device positioned at the venous end. In one embodiment, the valve devices may include an inflatable balloon that, when inflated, constricts and closes off the arteriovenous graft. If desired, a single actuator can be used to open and close both valve devices.

20 Claims, 14 Drawing Sheets

(56) References Cited

U.S. PATENT DOCUMENTS

| | | | |
|---|---|---|---|
| 2003/0127090 A1* | 7/2003 | Gifford | A61M 16/0057 128/200.24 |
| 2004/0168969 A1 | 9/2004 | Sternby et al. | |
| 2006/0079827 A1 | 4/2006 | Jensen et al. | |
| 2006/0129083 A1* | 6/2006 | Brenneman | A61B 17/12 604/9 |
| 2006/0224100 A1 | 10/2006 | Gertner | |
| 2006/0229548 A1 | 10/2006 | Cull | |
| 2014/0200558 A1* | 7/2014 | McDaniel | F16K 27/0227 604/544 |

OTHER PUBLICATIONS

Patent Cooperative Treaty International Search Report, dated Oct. 1, 2008. (2 pages).

* cited by examiner

ARTERIOVENOUS ACCESS VALVE SYSTEM AND PROCESS

CROSS-REFERENCE TO RELATED APPLICATIONS

The present application is a continuation of U.S. application Ser. No. 13/442,448 having a filing date of Apr. 9, 2012, which is, in turn, a continuation of U.S. application Ser. No. 11/807,479 having a filing date of May 29, 2007. Applicant claims priority to and the benefit of all such applications and hereby incorporates all such applications by reference herein in their entirety for all purposes.

BACKGROUND

The function of kidneys, which are glandular organs located in the upper abdominal cavity of vertebrates, is to filter blood and remove waste products. Specifically, kidneys separate water and waste products of metabolism from blood and excrete them as urine through the bladder. Chronic renal failure is a disease of the kidney in which the kidney function breaks down and is no longer able to filter blood and remove waste substances. Should certain toxic waste substances not be removed from the blood, the toxic substances may increase to lethal concentrations within the body.

Hemodialysis is a life-sustaining treatment for patients who have renal failure. Hemodialysis is a process whereby the patient's blood is filtered and toxins are removed using an extracorporeal dialysis machine. For hemodialysis to be effective, large volumes of blood must be removed rapidly from the patient's body, passed through the dialysis machine, and returned to the patient. A number of operations have been developed to provide access to the circulation system of a patient such that patients may be connected to the dialysis machine.

For example, the most commonly performed hemodialysis access operation is a subcutaneous placement of an arteriovenous graft, which is made from a biocompatible tube. The biocompatible tube can be made of, for instance, a fluoropolymer such as polytetrafluoroethylene. One end of the tube is connected to an artery while the other end is connected to a vein. The arteriovenous graft is typically placed either in the leg or arm of a patient.

Blood flows from the artery, through the graft and into the vein. To connect the patient to a dialysis machine, two large hypodermic needles are inserted through the skin and into the graft. Blood is removed from the patient through one needle, circulated through the dialysis machine, and returned to the patient through the second needle. Typically, patients undergo hemodialysis approximately four hours a day, three days a week.

Various problems, however, have been experienced with the use of an arteriovenous graft. For example, arterial steal occurs when excessive blood flow through the arteriovenous graft "steals" blood from the distal arterial bed. Arterial steal can prevent the proper supply of blood from reaching the extremity of a patient.

Various other complications can also occur. For instance, the blood flowing through the arteriovenous graft can often reach turbulent flow rates. This stream of fast moving blood then exits the arteriovenous graft and contacts the vein connected to the graft. This collision between the flow of blood and the vein may cause the development of myointimal hyperplasia which leads to the thickening of the vein walls and a narrowing of the vessel. As the vein narrows, flow through the arteriovenous graft decreases and blood within the graft may ultimately clot.

The cessation of blood flow through the graft caused by clot formation is known as graft thrombosis. Numerous techniques and medications have been studied in attempts to block the development of the scar tissue. Graft thrombosis, however, continues to remain a reoccurring complication associated with the use of arteriovenous grafts.

In view of the above drawbacks, a need currently exists in the art for an arteriovenous graft that can prevent and minimize arterial steal and graft thrombosis. A process for using an arteriovenous graft in minimizing arterial steal and graft thrombosis is also needed.

SUMMARY OF THE INVENTION

In general, the present invention is directed to subcutaneous arteriovenous graft systems and to processes for using the arteriovenous graft systems in a manner that eliminates or at least reduces arterial steal and graft thrombosis. In one embodiment, for instance, the system includes an arteriovenous graft having an arterial end and an opposite venous end. The arterial end is configured to be connected to an artery to form an arterial anastomosis, while the venous end is configured to be connected to a vein to form a venous anastomosis.

In accordance with the present invention, the system includes at least one valve device positioned at the arterial end of the arteriovenous graft. In one embodiment, for instance, the valve device comprises an inflatable balloon. The inflatable balloon is positioned so as to restrict blood flow through the arteriovenous graft when inflated. In general, the valve device should be positioned at the arterial end of the arteriovenous graft as close as possible to the intersection of the graft with an artery. For example, the valve device may be positioned so as to restrict blood flow through the arteriovenous graft at a location that is less than about 10 mm from the intersection of the arteriovenous graft and an artery.

The inflatable balloon of the valve device may have an annular shape that surrounds the arteriovenous graft. The inflatable balloon may also be a separate structure or may be integral with the arteriovenous graft. When integral with the arteriovenous graft, the arteriovenous graft may include a multi-layered segment located at the arterial end. The multi-layered segment may comprise an inner layer and an outer layer. The inner layer constricts the graft when a fluid is fed in between the inner layer and the outer layer. When having an annular shape, the balloon may be surrounded by a rigid collar that serves to assist the balloon in constricting the graft.

In an alternative embodiment, the valve device may include an inner sleeve and an outer sleeve. The inner sleeve may be attached to the outer sleeve except for over a discrete area. The discrete area can be in fluid communication with a fluid delivery device. When a fluid is fed to the discrete area, fluid is fed in between the inner sleeve and the outer sleeve causing the discrete area of the inner sleeve to inflate. In this embodiment, the discrete area, instead of surrounding the arteriovenous graft, can be circular or substantially circular in shape. When inflated, the discrete area forms a spherically shaped or a substantially spherically shaped balloon. In one embodiment, for instance, the outer sleeve may be more rigid than the inner sleeve. Thus, when the inner sleeve is inflated, the outer sleeve maintains its shape. In this embodiment, the balloon may be integral with the arteriovenous graft. Alternatively, the arteriovenous graft may be positioned within the inner sleeve.

In order to inflate and deflate the balloon, in one embodiment, the valve device can further include an injection port in fluid communication with the inflatable balloon. The injection port defines a diaphragm configured to receive a hypodermic needle for injecting fluid into or withdrawing fluid from the balloon. Of particular advantage, the injection port may also be subcutaneously implanted.

In an alternative embodiment, the inflatable balloon may be positioned in operative association with a piston. In this embodiment, when the balloon is inflated, the balloon forces the piston either towards or away from the arteriovenous graft for opening or closing the valve device.

When the valve device contains a piston, the valve device can include various configurations. Further, the piston can be used to inflate a balloon as described above or can be used to activate any other suitable structure configured to open and close the arteriovenous graft. In fact, in one embodiment, the piston itself may be used to open and close the graft.

In one embodiment, for example, the valve device may comprise a magnetically activated piston. In this embodiment, when a magnetic field is placed in close proximity to the valve device, the piston is moved for either opening or closing the valve device. For example, in one embodiment, placing a magnetic field in close proximity to the valve device opens the device which normally remains closed.

In one particular embodiment, the magnetically activated piston may be activated when exposed to a changing magnetic field, such as a pulsing magnetic field. In this embodiment, the valve device may include a coil member configured to convert a changing magnetic field into an electric current. The coil member is in communication with a solenoid. The solenoid is configured to move the piston and open or close the valve device when electric current is received from the coil member.

In an alternative embodiment, the valve device may include a piston that is biased towards a closed position. For example, a spring or other structure may apply a biasing force against the piston that maintains the piston in the closed position. In order to move the piston, the piston can be in operative association with a lever arm. When a magnetic field is placed in close proximity to the valve device, the lever arm may be configured to move causing the piston to move and open the valve device. In this embodiment, for instance, the piston may be in fluid communication with an inflatable balloon as described above. When the piston is moved into an open position, a fluid flows out of the balloon for deflating the balloon. When the piston is placed in the closed position, on the other hand, the fluid can be forced into the balloon for inflating the balloon.

In one embodiment, the arteriovenous graft system further includes a second valve device positioned at the venous end of the arteriovenous graft. The second valve device may be any suitable valve device as described above. The second valve device, for instance, may be identical to the first valve device or, alternatively, may be different.

The second valve device may be actuated using any suitable actuator. For instance, as described above, in one embodiment, the second valve device may include an inflatable balloon that is in fluid communication with an injection port. Alternatively, the second valve device may comprise an inflatable balloon that is in communication with a piston as described above.

In still another embodiment of the present disclosure, the subcutaneous arteriovenous graft system includes a first valve device positioned at the arterial end of the arteriovenous graft, a second valve device positioned at the venous end of the arteriovenous graft and a single actuator in communication with both the first valve device and the second valve device. The actuator is configured to open and close the valve devices simultaneously. The actuator may comprise, for instance, a fluid injection port, a piston as described above or any other suitable device. For instance, the injection port or the piston may be configured to deliver a fluid to each of the valve devices for inflating and deflating a balloon that closes and opens the valves respectively.

The second valve device may not be exposed or subjected to the same fluid pressures that are exerted on the first valve device. In this regard, the first valve device is designed to restrict or stop fluid flow at relatively high pressures. The second valve device, however, may be a low pressure valve device. In one embodiment, for instance, the second valve device may be a check valve positioned at the venous end of the arteriovenous graft. For example, the second valve device may be formed integral with the arteriovenous graft and may be formed from a membrane that allows fluid flow from the arteriovenous graft and into an adjoining vein but prevents fluid flow from the vein into the arteriovenous graft.

In an alternative embodiment, the check valve may comprise a pair of opposing and overlapping flaps positioned within the arteriovenous graft. The flaps can be integral with the graft or can be attached to the arteriovenous graft on opposing sides. For instance, the flaps can be attached to the graft using sutures or through a welding process. In order to prevent leakage, the check valve can further include edge seals that are positioned on opposing sides of each flap. The edge seals can create a seal with the radial wall of the arteriovenous graft.

The arteriovenous graft of the present invention is used for hemodialysis. During hemodialysis, two hypodermic needles are inserted into the arteriovenous graft. Blood is removed from the graft using one needle, circulated through a dialysis machine, and returned to the arteriovenous graft through the second needle. When hemodialysis is not being conducted, however, the valve devices of the present invention may be activated in order to minimize arterial steal and prevent thrombosis of the graft.

For example, in one embodiment of the present invention, when the arteriovenous graft system only includes a single valve device at the arterial end, after hemodialysis has ended, the valve device is closed thus preventing blood flow through the graft. After the valve device is closed, a blood compatible fluid may be injected into the graft using a hypodermic needle. As used herein, a blood compatible fluid refers to any fluid that is biocompatible with the circulation system, For example, in one embodiment, the blood compatible fluid is a heparinized saline solution. The saline solution is used to flush the graft after the valve device is closed in order to remove blood from the graft.

In another embodiment, after hemodialysis, the valve device is partially closed to a first position thereby constricting the arteriovenous graft and reducing blood flow through the graft. The patient is then monitored over a period of time, such as days or weeks, and the valve device may be selectively opened or closed from the first position until arterial steal is minimized. In this embodiment, the valve device is closed an amount sufficient to reduce blood flow through the graft without slowing the blood flow to a point where blood clots may form.

As described above, in another embodiment of the present invention, the arteriovenous graft system includes a first valve device at the arterial end and a second valve device at the venous end. In this embodiment, after hemodialysis has ended, the first valve device at the arterial end is closed thereby preventing blood flow through the graft. A hypodermic needle then flushes the graft with a blood compatible fluid evacuating all blood from the graft. After the graft has been flushed with the blood compatible fluid, the second valve device is then closed and the hypodermic needle is removed from the graft.

When the arteriovenous graft system contains first and second valve devices that are controlled by a single actuator, in one embodiment, the valve devices are opened so that there is blood flow through the graft. Two hypodermic needles are inserted into the graft and the blood is circulated through a dialysis machine. After hemodialysis has ended, the actuator is used to close both valve devices simultaneously. The arteriovenous graft can then be flushed. For instance, a fluid can be injected and removed from the graft using one or more hypodermic needles.

Other features and aspects of the present invention are discussed in greater detail below.

BRIEF DESCRIPTION OF THE DRAWINGS

A full and enabling disclosure of the present invention is set forth in the specification with reference to the following figures.

Reference now will be made to the embodiments of the invention, one or more examples of which are set forth below. Each example is provided by way of explanation of the invention, not as a limitation of the invention. In fact, it will be apparent to those skilled in the art that various modifications and variations may be made in the invention without departing from the scope or spirit of the invention. For instance, features illustrated or described as part of one embodiment may be used in another embodiment to yield a still further embodiment. For example, an arteriovenous graft system may include combinations of the valve devices described below. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied in the exemplary construction.

In general, the present invention is directed to an implantable arteriovenous graft system that may be used in carrying out hemodialysis treatments. Although the following description will refer to the arteriovenous graft system being implanted into an arm, it should be understood that the system may be implanted in any suitable location of the body. For example, in other embodiments, the arteriovenous graft system may be implanted into a leg.

In addition to being well suited for carrying out hemodialysis, the arteriovenous graft system of the present invention also prevents or minimizes arterial steal and graft thrombosis. In particular, the arteriovenous graft system is designed to prevent or minimize blood flow through the graft when hemodialysis is not occurring.

Figure 1:
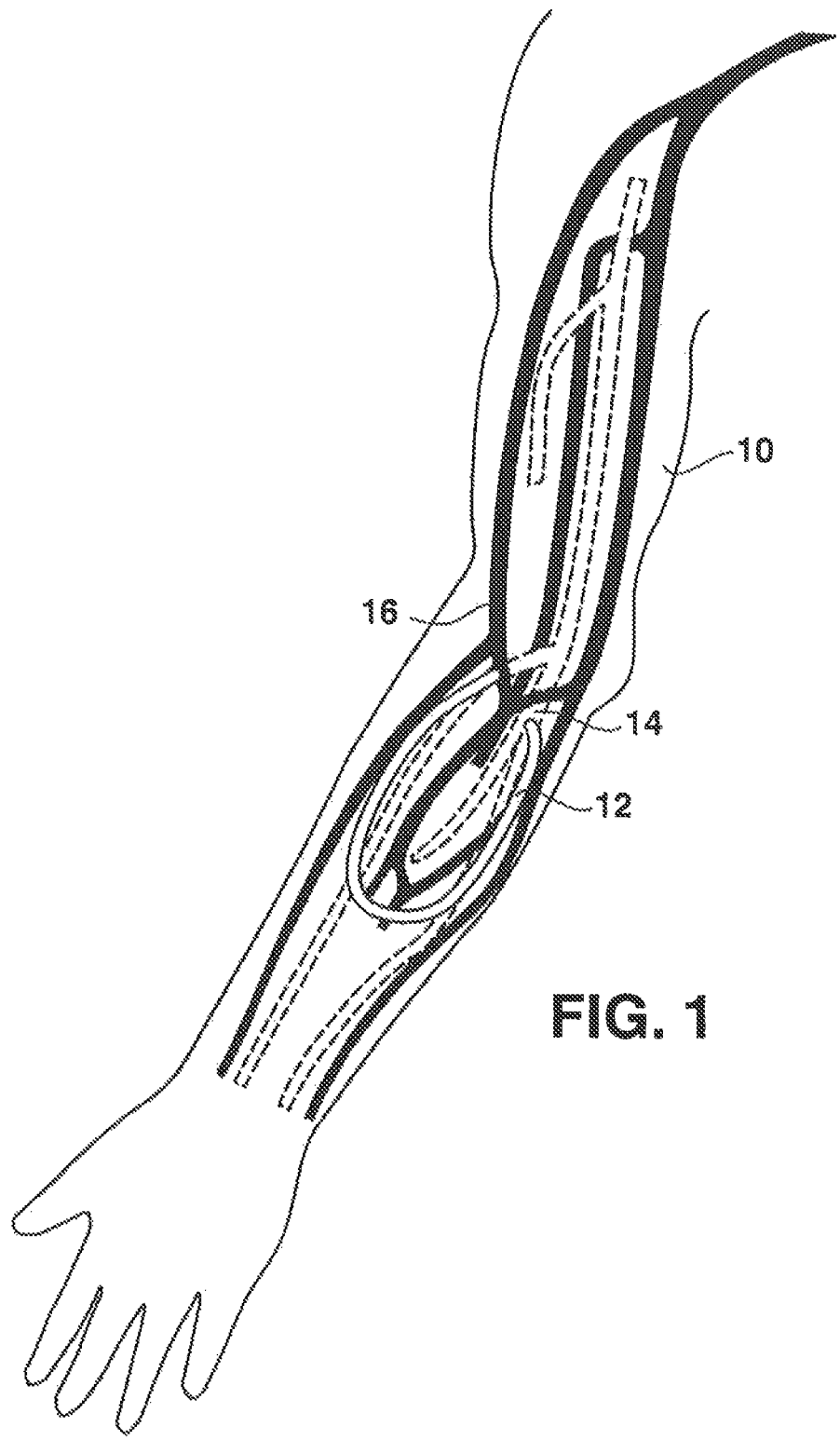
FIG. 1 is a side view with cut away portions of a human arm illustrating the placement of an arteriovenous graft.

Referring to FIG. 1, for purposes of explanation, a right arm 10 of a patient is shown. Selected arteries (shown as dotted pathways) are illustrated in conjunction with selected veins (shown as dark pathways). An arteriovenous graft 12 is shown connected at one end to an artery and at an opposite end to a vein. In particular, the arteriovenous graft 12 is connected to the brachial artery 14 and to the cephalic vein 16.

The arteriovenous graft 12 is made from any suitable biocompatible material. For example, in one embodiment, the graft is made from a fluoropolymer, such as polytetrafluoroethylene, which is commercially available as GOR-TEX™ from the W. L. Gore Company.

Figure 2A:
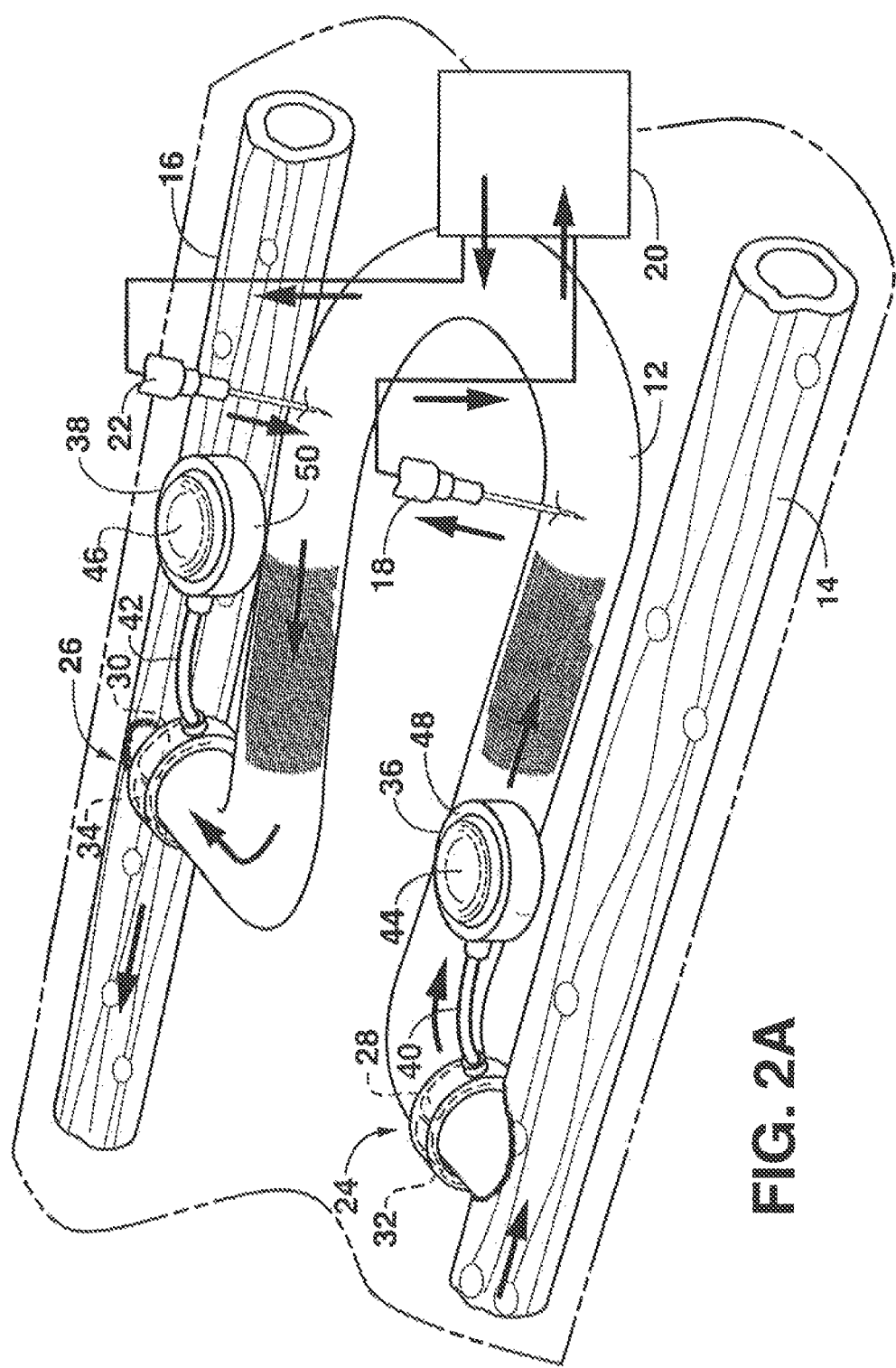
FIGS. 2A, 2B and 2C are perspective views of embodiments of arteriovenous graft systems made in accordance with the present invention.
Figure 2B:
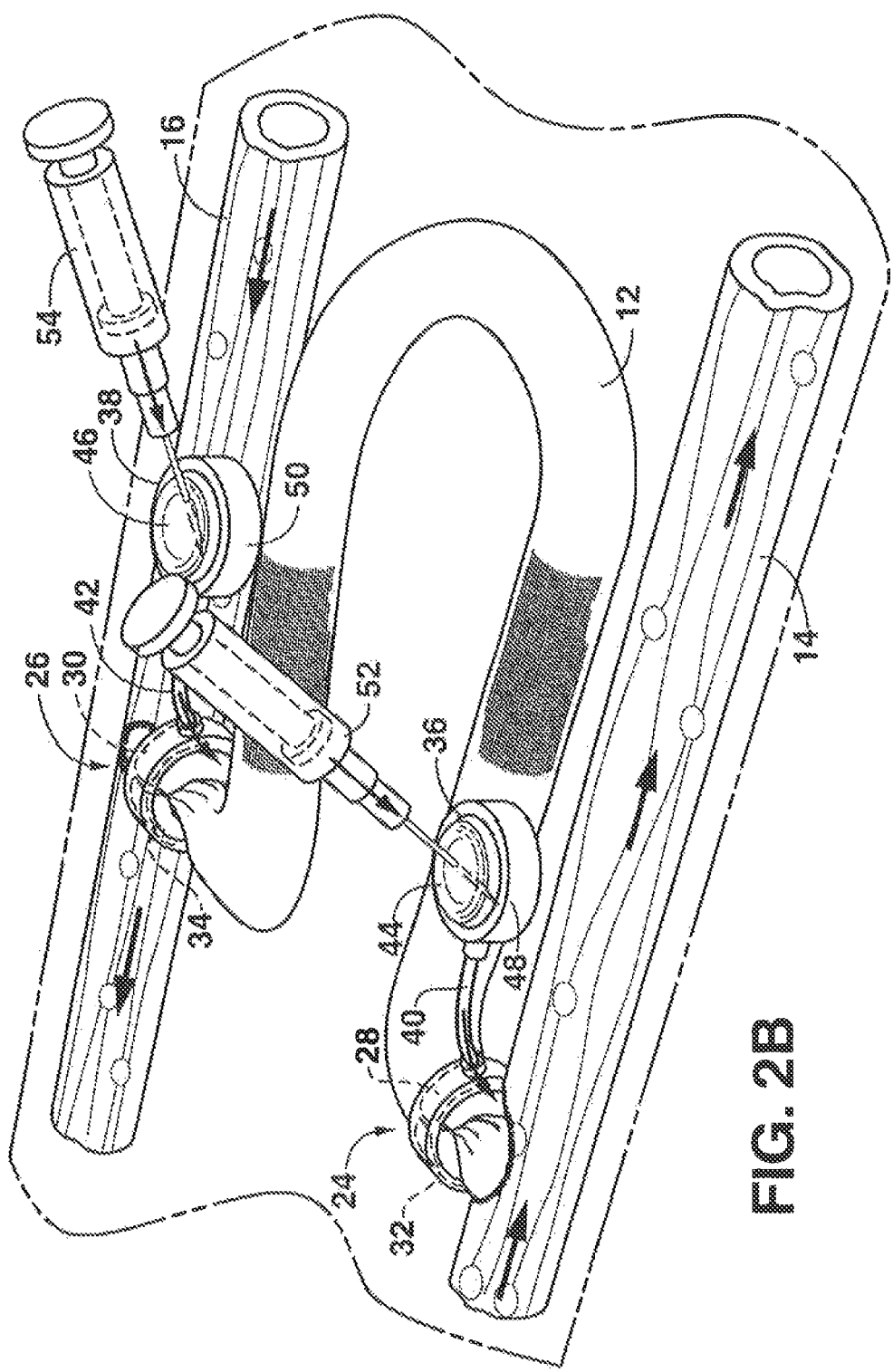

Referring to FIGS. 2A and 2B, one embodiment of an arteriovenous graft system made in accordance with the present invention is shown including an arteriovenous graft 12. As illustrated, the arteriovenous graft 12 is connected to an artery 14 and to a vein 16. In order to carry out hemodialysis, a first hypodermic needle 18 is inserted through the skin and into the arteriovenous graft 12. Blood is removed from the arteriovenous graft 12 through the needle and into a dialysis machine 20. In the dialysis machine, waste materials are removed from the blood. After circulating through the dialysis machine 20, the blood is then fed back into the arteriovenous graft 12 through a second hypodermic needle 22.

In accordance with the present invention, the arteriovenous graft system as shown in FIGS. 2A and 2B further includes at least a first valve device generally 24 positioned at the arterial end of the arteriovenous graft 12. Optionally, the arteriovenous graft system can further include a second valve device generally 26 positioned at the venous end of the arteriovenous graft. The valve devices 24 and 26 are in an open position during normal hemodialysis as shown in FIG. 2A. When hemodialysis has ended, however, the valve devices 24 and 26 are moved to a closed position in order to prevent blood flow through the arteriovenous graft. In this manner, arterial steal is either eliminated or reduced. Further, by reducing arterial steal, graft thrombosis is also prevented.

In addition to minimizing arterial steal and preventing graft thrombosis, the system and the process of the present invention also offer various other advantages. For example, reducing or stopping blood flow through the arteriovenous graft when hemodialysis is not occurring also prevents the graft from bleeding when the hypodermic needles used to carry out hemodialysis are removed from the graft. Hypodermic needles as shown in FIG. 2B, for instance, usually have a relatively large diameter or gauge. Thus, when the needles are removed from a graft, bleeding can occur where the needles have previously been. Needle hole bleeding through the graft can result in the formation of scar tissue and graft pseudoaneurisms. These complications, however, may be prevented through the use of the system of the present invention, In the embodiment shown in FIG. 2A, the valve devices 26 and 24 each include an inflatable balloon 28 and 30. When inflated, the balloons 28 and 30 constrict the arteriovenous graft 12 for reducing or eliminating blood flow through the graft.

As shown in FIG. 2A, the inflatable balloons 28 and 30, in this embodiment, have an annular shape that surround the arteriovenous graft 12. As shown, each of the inflatable balloons 28 and 30 are also surrounded by a rigid collar 32 and 34. Each collar 32 and 34 may be included in the system in order to maintain each of the balloons 28 and 30 in the proper position. Further, the collars 32 and 34 also serve to bias the balloon towards the arteriovenous graft 12 when inflated. Each collar 32 and 34 may be made from any rigid biocompatible material. For example, the collars 32 and 34 may be made from a metal, such as titanium, or a plastic material.

Figure 2C:
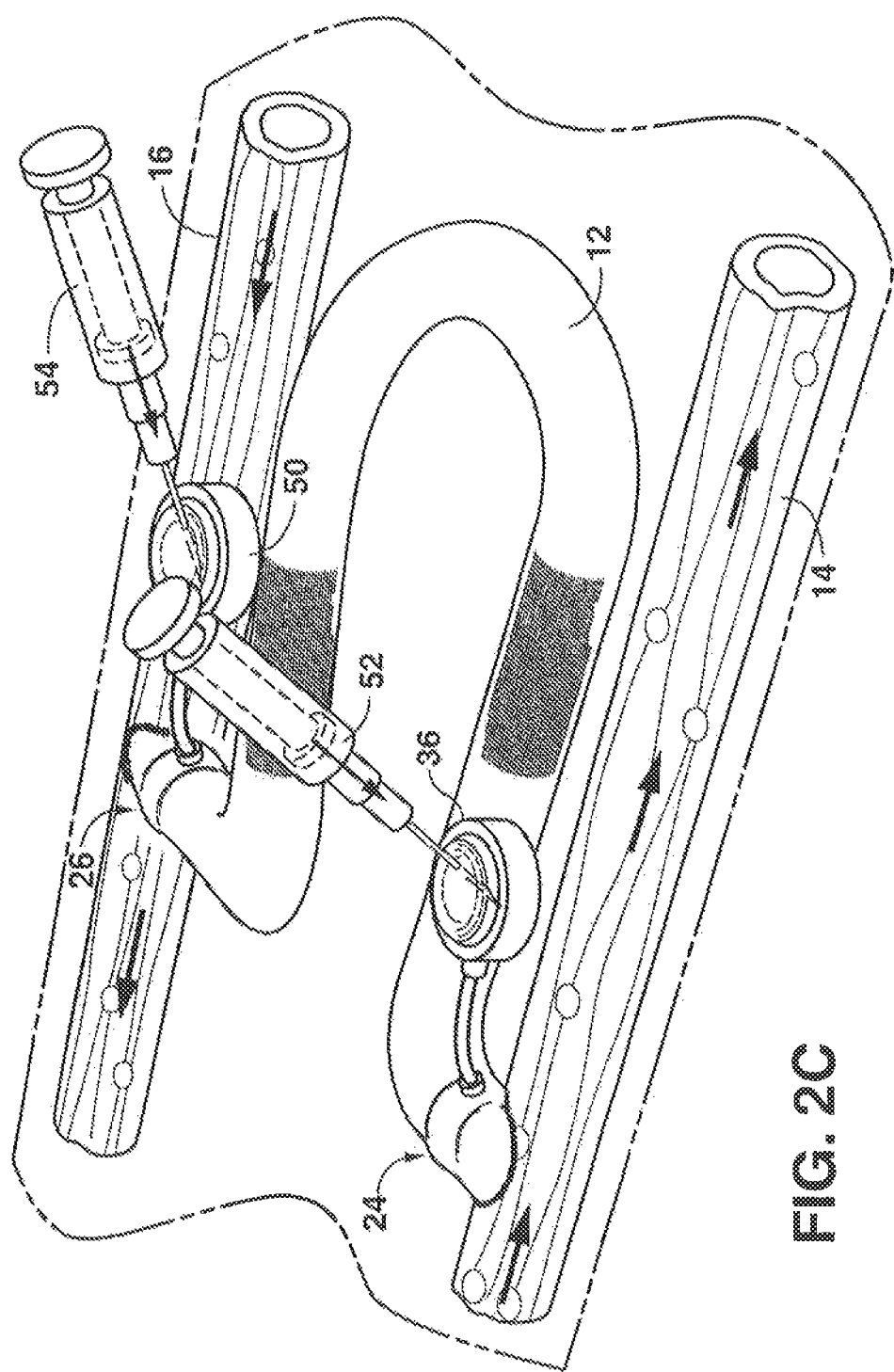

Each annular balloon 28 and 30 may be a separate structure from the arteriovenous graft 12 or may be integral with the graft. When integral with the graft, for instance, the graft may include a multi-layered segment where each of the valve devices is to be located. For example, within the multi-layered segment, the arteriovenous graft 12 may include an outer rigid layer and an inner luminal layer. The balloon 28 and 30 may be formed in between the outer layer and the inner layer. In particular, when a fluid is injected in between the inner and outer layers, the inner layer may expand and constrict the lumen. See FIG. 2C.

In addition to having an annular shape, it should be understood that each balloon 28 and 30 may have any shape sufficient to constrict the arteriovenous graft when inflated. For instance, in another embodiment, each balloon 28 and 30 may be located on one side of the graft 12. When inflated, the balloons 28 and 30 force opposite sides of the graft together.

Figure 6:
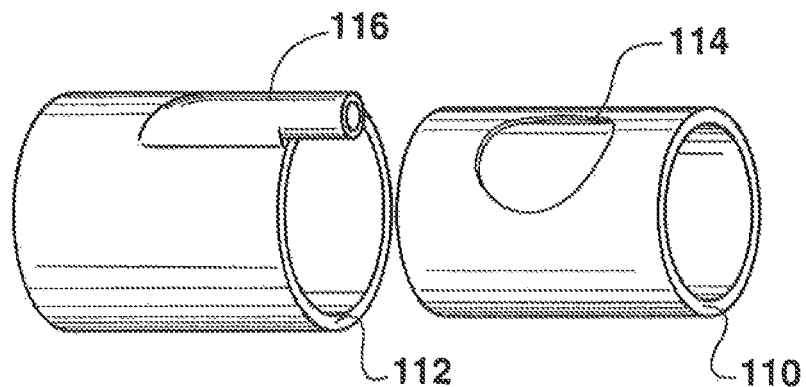
FIG. 6 is an unassembled perspective view of one embodiment of a balloon valve that may be used in accordance with the present disclosure.
Figure 7:
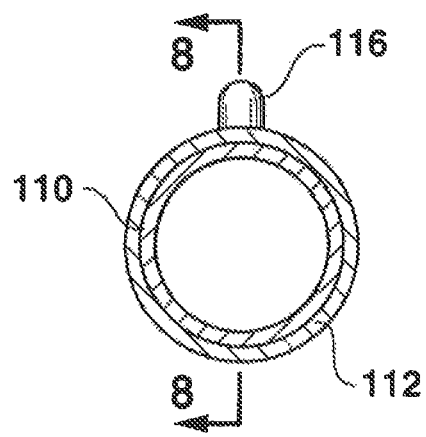
FIG. 7 is a cross-sectional view of the valve device illustrated in FIG. 6.
Figure 8:
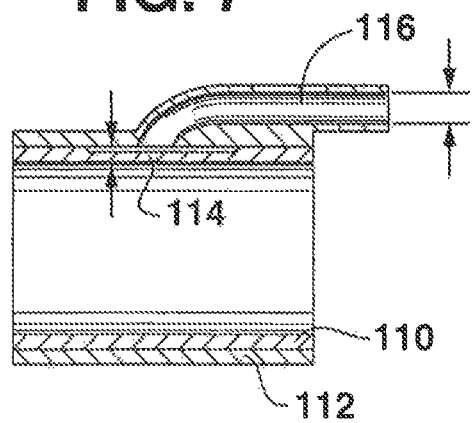
FIG. 8 is a cross-sectional view taken along line A-A of the valve device shown in FIG. 7.
Figure 9:
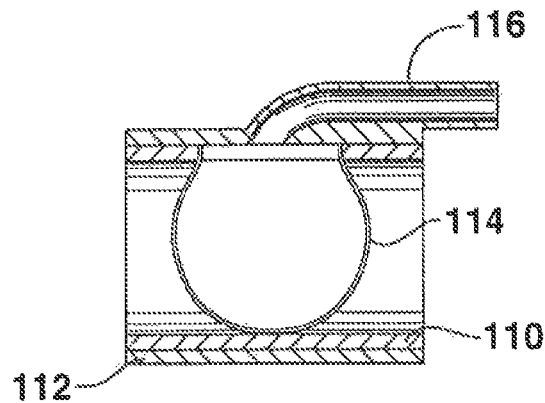
FIG. 9 is a cross-sectional view of the valve device illustrated in FIG. 6 showing the balloon inflated.

For example, referring to FIGS. 6 through 8, an alternative embodiment of a valve device containing an inflatable balloon is shown. As illustrated in FIG. 6, the valve device includes an inner sleeve 110 positioned within an outer sleeve 112. The inner sleeve can be attached or bonded to the outer sleeve at all locations except over a discrete area 114. As shown in FIGS. 7 and 8, the discrete area 114 is positioned opposite a fluid passageway 116. The fluid passageway 116 is placed in communication with a fluid delivery device. When fluid is forced through the fluid passageway 116, the fluid causes the discrete area 114 to inflate and form a balloon as shown in FIG. 9.

The inner and outer sleeves can be made from various materials and can be formed using various techniques. In one embodiment, for instance, the inner and outer sleeves can be injection molded and bonded together. For example, both the inner sleeve and the outer sleeve may be made from a suitable elastomer, such as a silicone elastomer. The outer sleeve 112 can be made more rigid than the inner sleeve 110 so that the outer sleeve preserves its shape when the discrete area 114 is inflated. The outer sleeve 112 can be made more rigid by having a greater thickness or by being made from a stiffer material, such as a material that has a higher durometer in comparison to the material used to form the inner sleeve.

In order to attach the inner sleeve 110 to the outer sleeve 112, any suitable technique may be used. For example, in one embodiment, an adhesive material, such as an adhesive material containing a silicone elastomer may be used to bond the two layers together. In other embodiments, the two layers may bond together during the molding process.

As shown in FIG. 8, in one embodiment, the discrete area 114 may have a thickness that is less than the thickness of the remainder of the inner sleeve 110. For instance, the discrete area 114 may have a thickness of less than about 0.015 inches. As shown in FIG. 6, in one embodiment, the discrete area 114 may have a circular or a substantially circular shape. By having a substantially circular shape, the discrete area expands uniformly and inflates evenly across its plane during inflation, thus minimizing stress on the material. Once inflated as shown in FIG. 9, the discrete area 114 can have a spherical or substantially spherical shape. The inflated shape can compress the arteriovenous graft and prevent leakage. The substantially spherical shape also allows the balloon to be inflated to a size and pressure which can assure constriction and sealing of a 200 mmHg pressure gradient across the graft. The balloon can also be designed to be overpressurized by greater than about 30% thus serving as a safety factor. Ultimately, the design is free of bulk, pinch points which minimizes patient discomfort.

The valve device as shown in FIGS. 6 through 9 can be integral with the arteriovenous graft or the arteriovenous graft can fit inside the inner sleeve 110. In one embodiment, the inner and outer sleeves can be slit along the length in order to facilitate installation over a graft. Once installed over a graft, the slit formed in the valve device can be connected together through thermal bonding, clips or sutures.

In order to inflate the balloons as shown in the figures, in one embodiment as shown in FIGS. 2A and 2B, each valve device may further include an injection port 36 and 38. For example, as shown in FIG. 2A, injection port 36 may be in fluid communication with the balloon 28 via a tubing 40. Similarly, injection port 38 may be in fluid communication with the balloon 30 via a tubing 42. Each injection port 36 and 38 may be configured to be subcutaneously implanted in a patient.

In the embodiment illustrated in FIG. 2A, injection ports 36 and 38 each include a diaphragm 44 and 46 positioned on one side of a housing 48 and 50. The housings 48 and 50 may be made from any suitable rigid and biocompatible material. For example, each housing may be made from a metal, such as titanium. Each diaphragm 44 and 46, on the other hand, may be made from a material capable of receiving the tip of a hypodermic needle. For example, each diaphragm 44 and 46 may be made from an elastomeric film, such as a silicone membrane.

As shown particularly in FIG. 2B, in order to inflate or deflate the balloons 28 and 30, hypodermic needles 52 and 54 may inject a fluid into each of the injection ports 36 and 38 through the diaphragms 44 and 46. The fluid travels from the injection ports 36 and 38 through the tubing 40 and 42 and into each respective balloon 28 and 30. Similarly, the hypodermic needles 52 and 54 may also be used to withdraw fluid from the balloons 28 and 30.

As shown in FIG. 2B, once inflated, the balloons 28 and 30 constrict the arteriovenous graft 12 at the arterial end and at the venous end. The fluid used to inflate the balloons 28 and 30 may vary depending upon the particular application. The fluid may be, for instance, a gas or liquid. In one embodiment, for instance, a saline solution may be injected into the injection ports 36 and 38 for inflating the balloons. In one embodiment, it may take from about 2 ccs to about 6 ccs of fluid to transition each balloon valve 28 and 30 from an open position to a closed position.

When closed, each valve device should be capable of maintaining its position when exposed to systolic pressure. For example, systolic pressures in arteries may be greater than about 250 mmHg, such as from about 170 mmHg to about 270 mmHg, In addition to withstanding relatively high fluid pressures, each of the valve devices 24 and 26 should also be constructed so that the valve devices can constrict the arteriovenous graft as close as possible to the intersection of the graft with the artery 14 and the vein 16. For example, the first valve device 24, in one embodiment, constricts the arteriovenous graft at a distance of from about 5 mm from the arterial anastomosis, such as no greater than about 20 mm from the arterial anastomosis. The position of the second valve device 26 in relation to the venous anastomosis may also be within the above defined limits.

The methods for using the arteriovenous graft system of the present invention will now be discussed in relation to a system that contains a single valve device positioned at the arterial end of the graft and a system that contains two valve devices as shown in FIGS. 2A and 2B.

When the arteriovenous graft system of the present invention contains a single valve device positioned at the arterial end, in one embodiment, the valve device may be positioned so as to constrict blood flow through the graft when hemodialysis is not occurring. In this embodiment, arterial steal is not being completely prevented but is being minimized. In particular, the single valve device constricts the graft so that blood flow through the graft continues without clotting but is at a reduced flow rate.

In this embodiment, the patient's condition may need to be monitored over a period of time, such as days or weeks, and the valve device may be adjusted in order to minimize arterial steal without causing a complete blood stoppage. For instance, over several days or weeks, the arteriovenous graft of the patient may be monitored and the valve device may be adjusted so as to gradually increase or decrease the narrowing of the arteriovenous graft. The ultimate position of the valve will vary depending upon the patient and the location of the arteriovenous graft.

In an alternative embodiment, the single valve device may be used to completely close off the arteriovenous graft 12 at the arterial end. In this embodiment, during hemodialysis, the valve device 24 is in the open position and the arteriovenous graft 12 is cannulated with the two dialysis needles 18 and 22 as shown in FIG. 2A. Upon completion of dialysis, a fluid is injected into the injection port 36 of the first valve device causing the balloon 28 to inflate thereby closing the valve device and eliminating arterial blood flow through the graft.

After the valve device is closed, a blood compatible fluid is then injected into the arteriovenous graft 12 through, for instance, a dialysis needle to flush any residual blood out of the graft. The blood compatible fluid can be, for instance, heparinized saline. The residual blood is flushed out of the graft in order to prevent any clotting.

In this embodiment, some residual saline remains in the graft until hemodialysis is once again conducted on the patient. This embodiment should only be used when it is determined that substantially no blood from the vein 16 will flow into the graft once valve device 24 is closed.

In order to prevent any blood flowing from the vein 16 back into the arteriovenous graft 12 after the first valve device 24 has been closed, in one embodiment of the present invention as shown particularly in FIGS. 2A and 2B, the arteriovenous graft system can include the second valve device 26. In this embodiment, the process as described above is repeated. After the arteriovenous graft 12 is flushed with a blood compatible fluid, however, a fluid is injected into the injection port 38 of the second valve device 26 which causes the second valve device to close.

In addition to the valve devices as illustrated in FIGS. 2A and 2B, in other embodiments, other valve devices may also be utilized in the system of the present invention. For example, referring to FIG. 4, another embodiment of a valve device generally 60 is shown in communication with an arteriovenous graft 12. In this embodiment, the valve device 60 includes a fluid chamber 62 in communication with an injection port 64 similar to the injection ports described above. As shown, injection port 64 includes a diaphragm 68 configured to receive fluid from a hypodermic needle 70.

The valve device 60 further includes a piston 72 contained within a housing 74. The piston 72 is positioned below the fluid chamber 62.

In this embodiment, when a fluid is injected from the needle 70 into the injection port 64, the fluid is forced into the fluid chamber 62 via a tube 66. The pressure of the fluid then forces the piston 72 to lower closing the valve and constricting flow through the arteriovenous graft 12.

Figure 4:
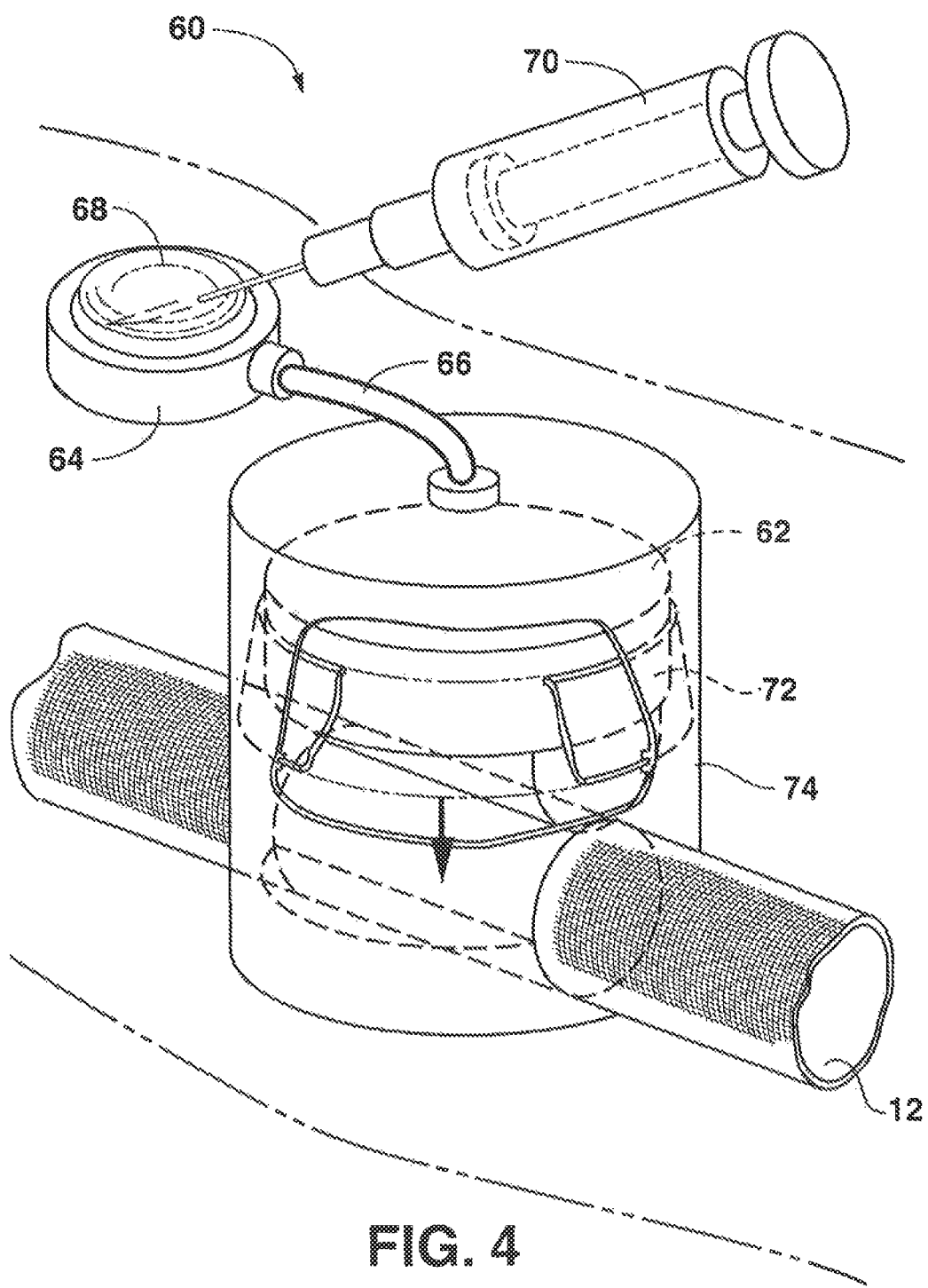
FIG. 4 is a perspective view of another embodiment of a valve device that may be used in the arteriovenous graft system of the present invention.

Valve device 60 as shown in FIG. 4 may be used in a single valve system of the present invention or in a double valve system of the present invention as illustrated in FIG. 2A.

Figure 3:
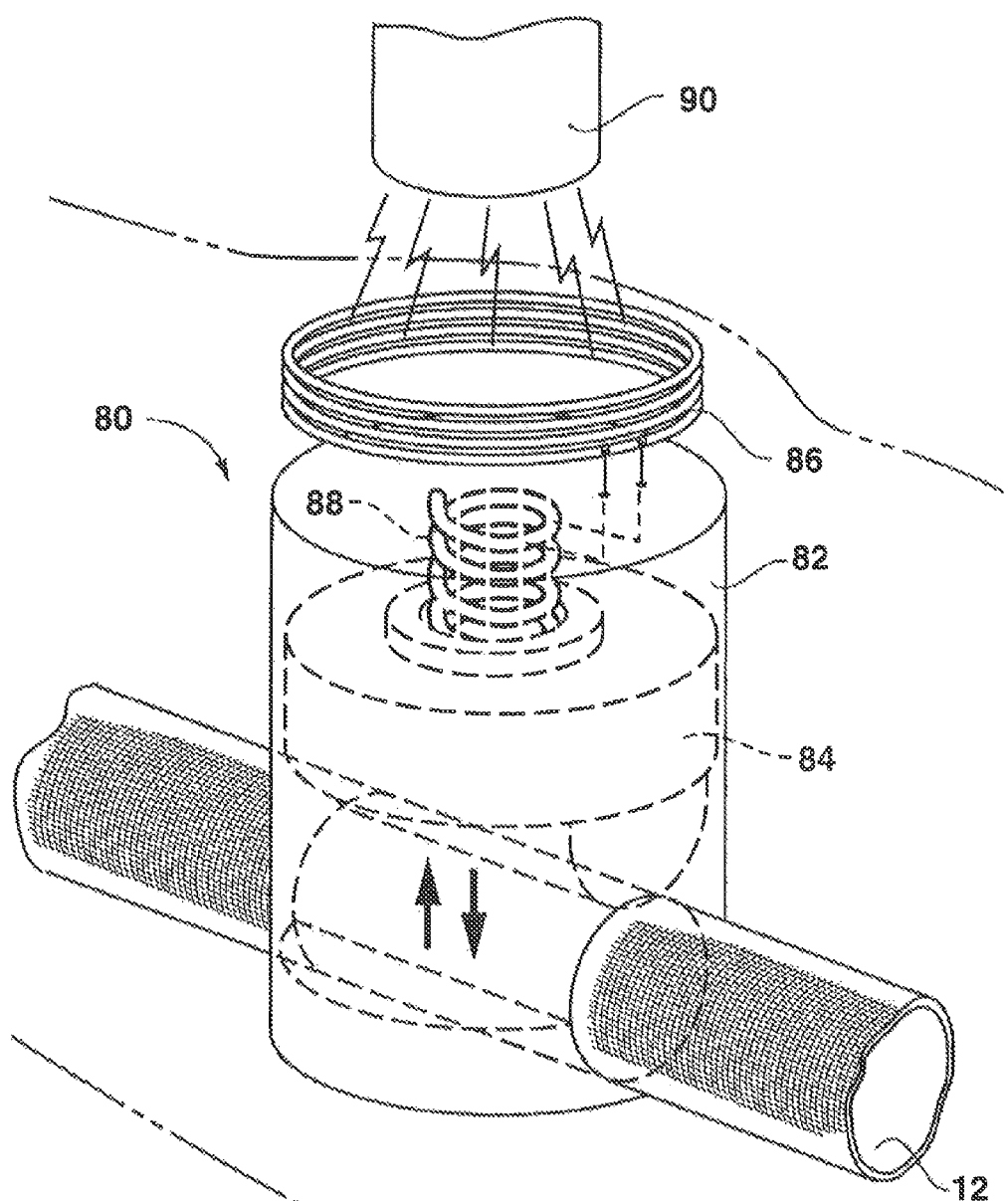
FIG. 3 is a perspective view of one embodiment of a valve device that may be used in the arteriovenous graft system of the present invention.

Referring to FIG. 3, another embodiment of a valve device generally 80 that may be used in the arteriovenous graft system of the present invention is illustrated. In this embodiment, the valve device 80 includes a housing 82 containing a magnetically actuated piston 84. Specifically, the valve device is configured such that the piston 84 moves between an open and closed position when the valve device is contacted with a magnetic field.

In this particular embodiment, the valve device 80 includes a coil member 86. The coil member 86 is configured to convert a pulsating magnetic field into an electric current. As shown, the coil member 86 then supplies the electric current to a solenoid 88. Solenoid 88 then moves the piston 84 to either open or close the valve device.

In order to activate the valve device 80, a magnetic key 90 is placed close to the skin of a patient. In this embodiment, the magnetic key 90 may be an electromagnet that creates a pulsating magnetic field. As described above, the pulsating magnetic field is then converted into an electric current by the coil member 86. The magnetic key 90 may be configured either to open or to close the valve device. In one embodiment, for instance, the valve device 80 may normally be found in a closed position blocking off the arteriovenous graft 12. When the magnetic key 90, however, is placed adjacent to the patient's skin, the valve device 80 then opens allowing blood to circulate through the graft. In other embodiments, however, it should be understood that the valve device may be configured to close when placed adjacent to the magnetic key 90.

In addition to the valve device 80 as shown in FIG. 3, other magnetically activated valves may be used in the system of the present invention. For example, in another embodiment of the present invention, the valve device may include a piston in operative association with a permanent magnet. A ferrous plate may be positioned on the opposite side of the arteriovenous graft. Thus, the permanent magnet contained in the piston is attracted to the ferrous surface for closing off the arteriovenous graft. When a magnet with opposite polarity, however, is placed adjacent to the valve device, the permanent magnet contained within the piston is attracted to the reverse magnetic field causing the valve to open.

Figure 10:
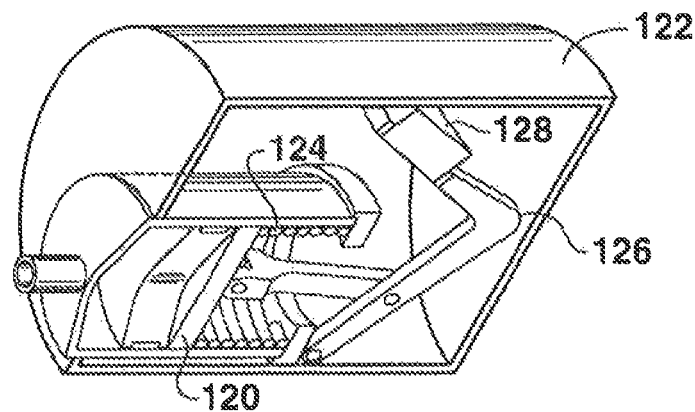
FIG. 10 is a perspective view with cut away portions showing another embodiment of a valve device that may be used in accordance with the present disclosure.

Referring to FIGS. 10 through 13, still another embodiment of a magnetically activated valve device that may be used in accordance with the present disclosure is shown. In this embodiment, the valve device includes a magnetically activated piston 120 as shown in FIG. 10. As illustrated, the piston 120 is contained within a housing 122. The piston is biased towards a closed position by a spring 124. In particular, the spring 124 applies a biasing force to the piston 120.

Figure 11:
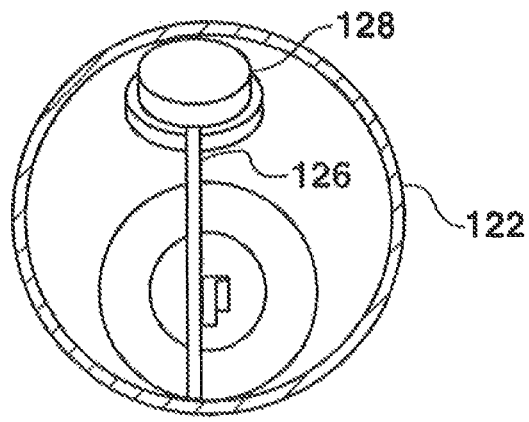
FIG. 11 is a cross-sectional view of the valve device illustrated in FIG. 10.

As shown in FIGS. 10 and 11, the piston is also attached to a lever arm 126. The lever arm 126 is attached to a magnet member 128 or a magnetically attractable member 128. In this embodiment, when an external key comprising a magnet or an electromagnet is placed adjacent to the member 128, the lever arm 126 moves which in turn causes the piston to move and open or close the valve.

In the embodiment shown in the figures, the piston 120 is normally biased in a closed position. When a magnetic key is placed adjacent to the valve device, the lever arm causes the piston 120 to move and open the valve device. It should be understood, however, that in other embodiments the lever arm may be used to close the valve.

Figure 12:
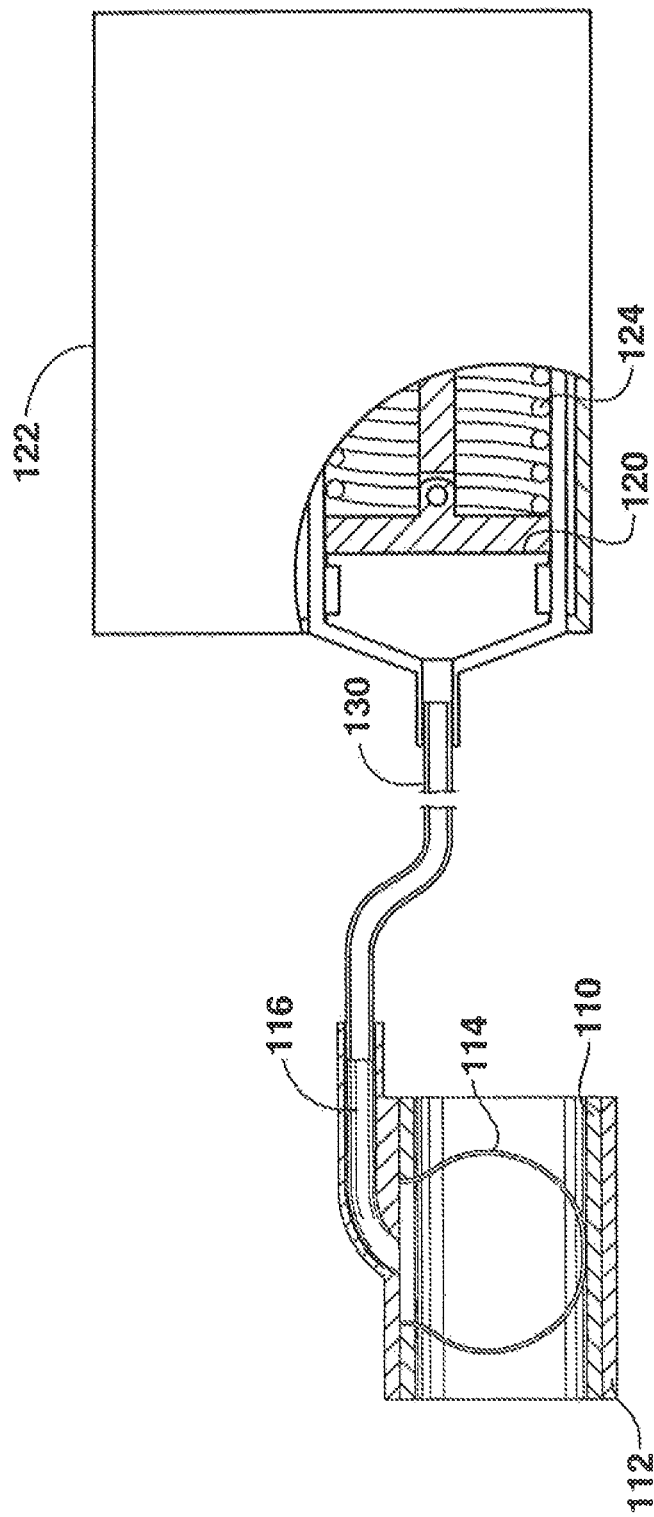
FIG. 12 is a side view with cut away portions illustrating the valve device shown in FIG. 10 in association with a balloon.

The piston 120 as shown in FIG. 10 can be placed in association with an arteriovenous graft in order to open and close the graft. In one particular embodiment as shown in FIG. 12, for example, the piston 120 can be placed in communication with a balloon valve such as the one illustrated in FIGS. 6 through 9. In this embodiment, the piston 120 is used as a fluid delivery device that delivers fluid to the balloon.

For instance, referring to FIG. 12, the piston 120 is shown in a closed position caused by a biasing force being placed against the piston by the spring 124. When in the closed position, the piston 120 forces a fluid through the conduit 130 and in contact against the discrete area 114, causing the discrete area to inflate and form a substantially spherical shape. When inflated, the discrete area 114 blocks flow through the arteriovenous graft.

Figure 13:
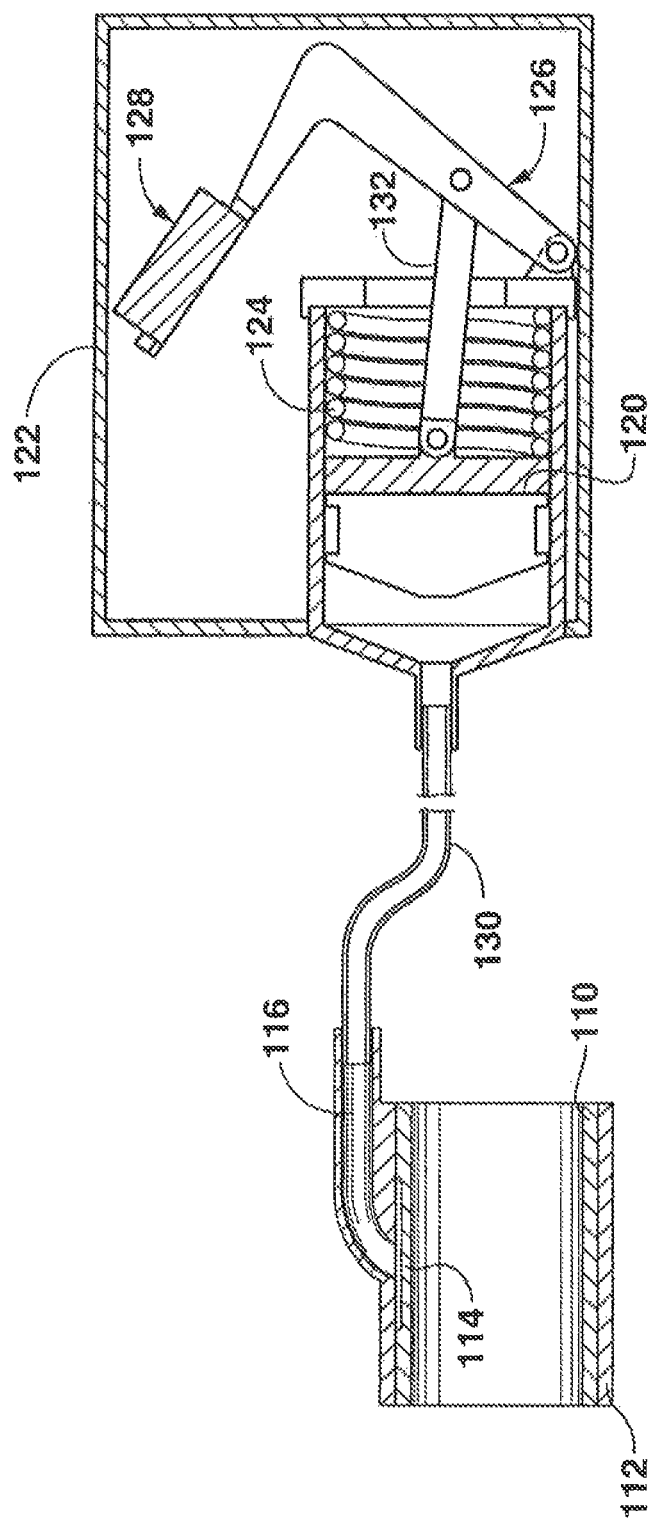
FIG. 13 is a cross-sectional view of the valve device illustrated in FIG. 12 illustrating the balloon being deflated.

When it is desired to open the arteriovenous graft for dialysis treatment, for instance, a key comprising a magnet or an electromagnet is placed adjacent to the valve device. Referring to FIG. 13, for instance, the magnetic or electromagnetic key is placed adjacent to the magnetic member or magnetically attractable member 128 causing the lever arm 126 to pivot or move. The lever arm 126 is attached to a linking member 132 that is in turn connected to the piston 120. When the lever arm 126 is pivoted, the linking member 132 causes the piston to retract as shown. Fluid contained within the conduit 130 is thereby drawn out of the discrete area 114 causing the balloon to deflate. In this manner, the valve device is opened for allowing blood flow through the arteriovenous graft. During the dialysis treatment, the external magnetic key can be fixed into position to ensure that the valve device stays open. For instance, the external key can be taped or otherwise attached to the skin of the patient. When the dialysis treatment is concluded, the external magnetic key is removed and the valve device automatically returns to the closed position.

The fluid that is contained within the valve device may vary depending upon the particular application and the desired results. In one embodiment, for instance, a saline solution may be contained within the valve device.

In the embodiment illustrated in the drawings, the lever arm 126 is moved based upon an attracting magnetic force. It should be understood, however, that magnetic repulsion can also be used to move the lever arm as well.

The valve device as shown in FIGS. 10 through 13 can be designed to be relatively small for being implanted under the skin of a patient. For instance, the housing 122 as shown in FIG. 10 can have a diameter less than about 3 cm and can have a height of less than about 1 cm.

Using a magnetically actuated valve device as shown in FIGS. 10 through 13 can provide various advantages. For instance, because the valve device is magnetically actuated, the valve device eliminates the need to use hypodermic needles for transferring liquid into and out of a plenum or port.

In still another embodiment, the valve device as shown in FIGS. 10 through 13 may be actuated other than through use of a magnet. For instance, in one embodiment, the valve device may include a pump in communication with a battery. The pump may be turned on and off using wireless telemetry. In fact, wireless telemetry may also deliver real time pressure measurements thereby communicating the status of the valve device.

Figure 19:
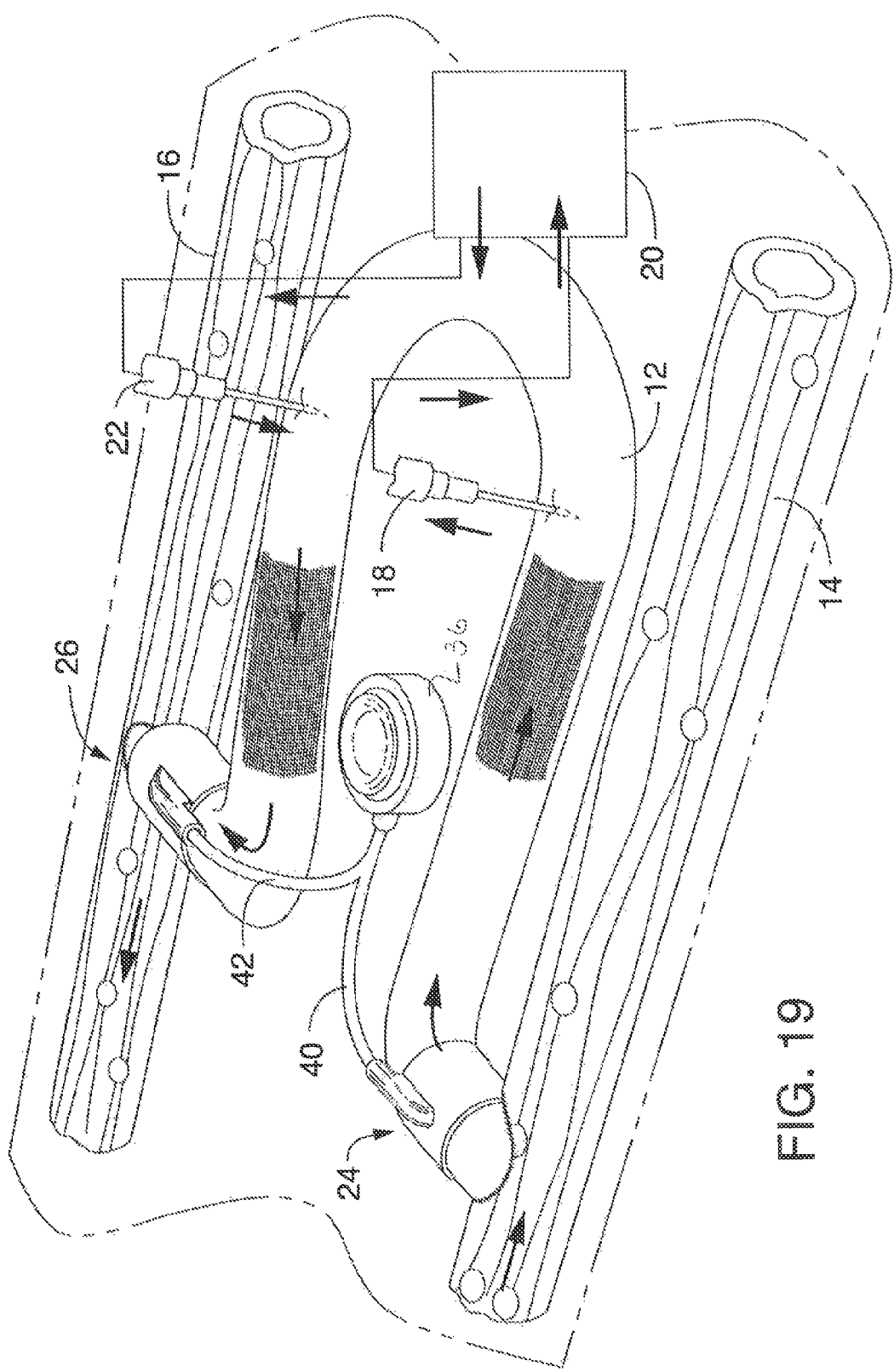
FIG. 19 is a perspective view of yet another alternative embodiment of an arteriovenous graft system in accordance with the present disclosure, Repeat use of reference characters in the present specification and drawings is intended to represent the same or analogous features of the invention.

Another embodiment of an arteriovenous graft system in accordance with the present disclosure is illustrated in FIG. 19. Like reference numerals have been used to identify similar features and elements of other embodiments. As shown, the system illustrated in FIG. 19 is similar to the embodiment illustrated in FIG. 2A. As shown, the system includes an arteriovenous graft 12 that is connected to an artery 14 at one end and to a vein 16 at an opposite end. In accordance with the present disclosure, the system includes a first valve device 24 positioned at the arterial end and a second valve device 26 positioned at the venous end of the graft. The first valve device 24 and the second valve device 26 are constructed similar to the valve devices illustrated in FIGS. 6-9. It should be understood, however, that any suitable valve device can be positioned at either end of the graft. Further, the first valve device can be the same or can be different from the second valve device.

In the embodiment illustrated in FIG. 19, the first valve device 24 and the second valve device 26 are both connected to a single actuator 36. The actuator 36 is configured to open and close both valve devices simultaneously. For example, in the embodiment illustrated, the actuator 36 comprises a fluid port that is in communication with the first valve device 24 via tubing 40 and is in communication with the second valve device 26 via tubing 42. When a fluid is injected or withdrawn from the port 36, both valve devices close or open respectively.

Various benefits and advantages may be realized by only having a single actuator for both valve devices as shown in FIG. 19. For instance, only having a single actuator simplifies the system and only requires that a single actuator be implanted within a patient. Further, in some applications, there may be advantages to having the valve devices open and close simultaneously.

The actuator 36 as shown in FIG. 19 comprises an injection port. It should be understood, however, that any suitable valve actuator may be installed within the system. For instance, in an alternative embodiment, the actuator 36 may comprise a piston such as shown in FIGS. 10-13 that may be configured to inflate and deflate a balloon contained within the valve devices. In still another embodiment, the actuator 36 may comprise a solenoid that is configured to electrically open and close the valve devices.

In order to carry out hemodialysis, a first hypodermic needle 18 and a second hypodermic needle 22 are shown inserted into the arteriovenous graft 12. When the valve devices 24 and 26 are open, blood can circulate from the graft into the first hypodermic needle 18, through the dialysis machine 20 and back into the graft through the hypodermic needle 22.

In one embodiment, the valve devices 24 and 26 are normally configured to be in a closed position. In order to open the valve devices and permit blood flow through the graft, fluid can be removed through the actuator 36 causing the balloons in the valve devices to deflate. Once both valve devices are open, the dialysis process can be carried out.

Once a sufficient amount of blood has been circulated through the dialysis machine, fluid can then be inserted into the actuator 36 for simultaneously closing the valve devices 24 and 26. Closing the valve devices stops blood flow through the graft. After hemodialysis is complete, the graft 12 can be flushed. For instance, a blood compatible fluid can be circulated through the graft using a single hypodermic needle or through the use of two hypodermic needles. In one particular embodiment, for instance, one hypodermic needle can be used to insert a blood compatible fluid, such as a saline solution, through the graft while a second needle can be used to remove the fluid.

Figure 5:
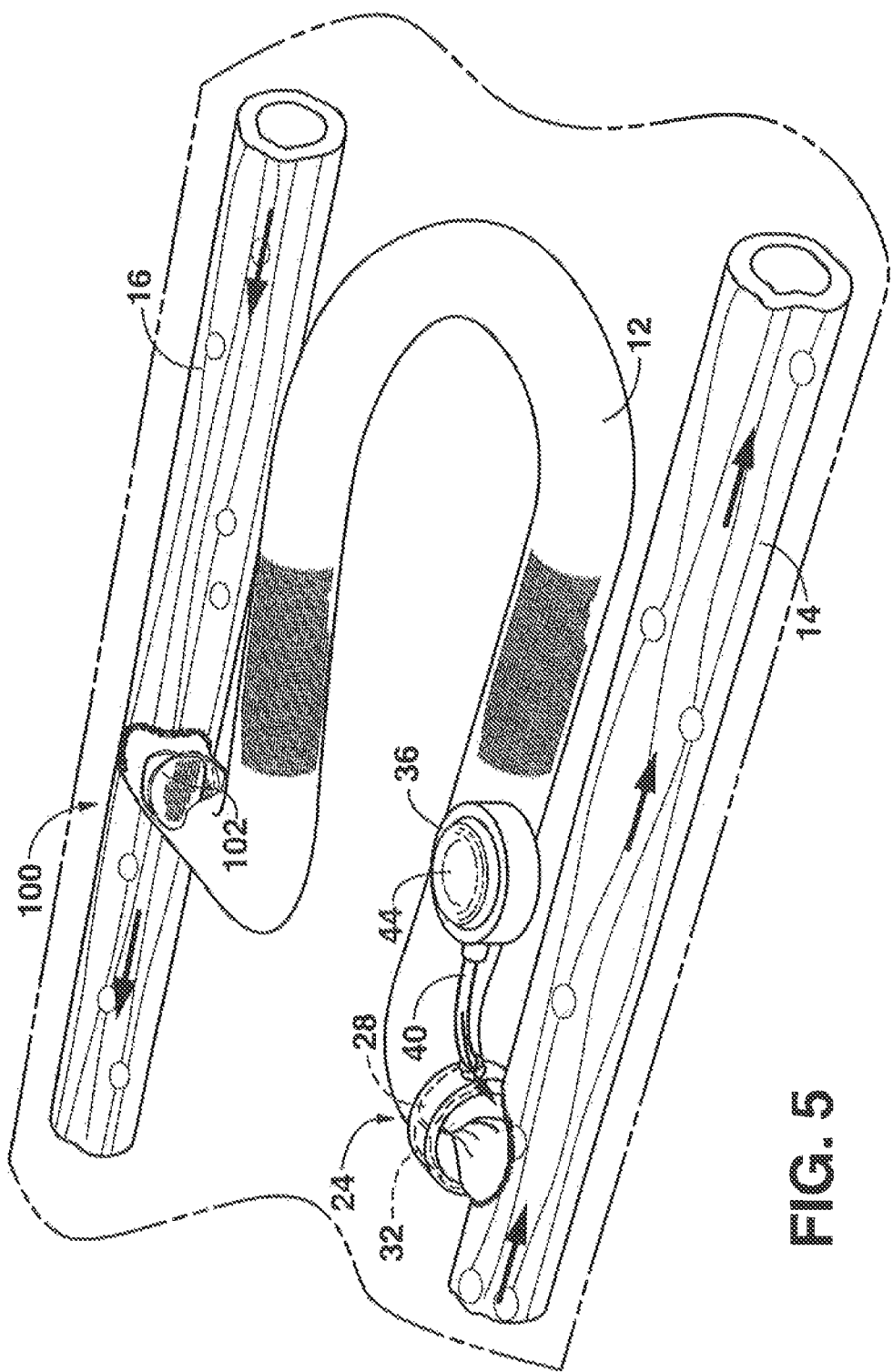
FIG. 5 is a perspective view of still another embodiment of an arteriovenous graft system made in accordance with the present invention.

Referring to FIG. 5, another embodiment of an arteriovenous graft system made in accordance with the present invention is shown. Like reference numerals have been used in order to identify similar features and elements of other embodiments. As shown, in this embodiment, the arteriovenous graft system includes a first valve device generally 24 at the arterial end of the graft similar to the valve device shown in FIGS. 2A and 2B. In particular, the first valve device 24 includes a balloon 28 that is inflated or deflated using an injection port 36. The balloon 28 is for constricting the arteriovenous graft when desired. As explained above, the first valve device 24, for most applications, is capable of maintaining a closed or constricted position on the graft even when exposed to relatively high fluid pressures. In some embodiments, however, these same pressures are not experienced at the venous end of the graft.

In this regard, in this embodiment, the arteriovenous graft 12 includes a second valve device generally 100 that may be described as a low pressure valve device when compared to the first valve device 24.

For example, in one embodiment, the second valve device 100 may be a check valve that allows fluid flow from the graft 12 into the vein 16 but does not permit flow from the vein 16 into the graft 12. In general, any suitable check valve may be used in accordance with the present invention.

In the embodiment shown in FIG. 5, the second valve device 100 includes a membrane 102 made from, for instance, a polymeric film that is formed or is connected so as to be integral with the arteriovenous graft 12. The membrane 102 may be, for instance, a flap that allows fluid flow in one direction from the graft 12 into the vein 16. The membrane 102 may be formed from a single piece of film or may be formed from multiple segments. For example, in one embodiment, the film can include one or more slits that permit fluid flow in one direction.

The arteriovenous graft system in FIG. 5 provides various advantages. For example, in the embodiment shown in FIG. 5, only the first valve device 24 needs to be manually opened or closed.

In the embodiment shown in FIG. 5, the first valve device is represented as a balloon valve. It should be understood, however, that the first valve device may be any of the other valve devices shown and described above.

Figure 14:
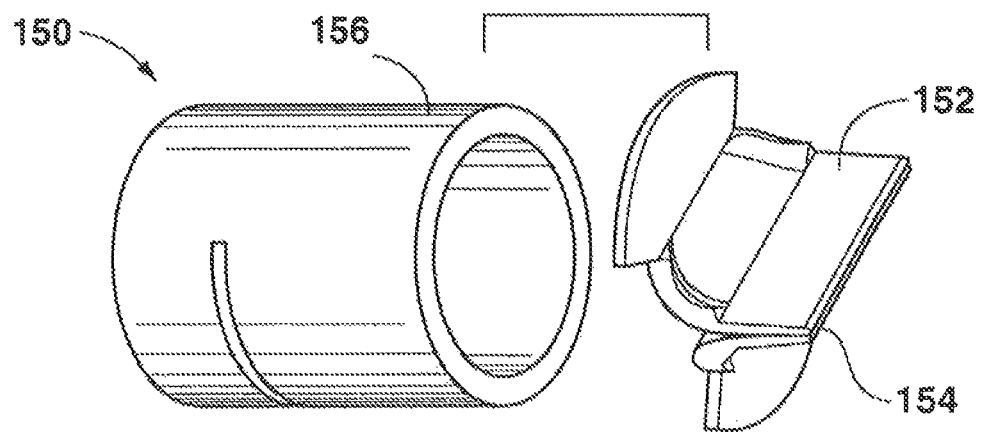
FIG. 14 is an unassembled perspective view of one embodiment of a check valve that may be used in accordance with the present disclosure.
Figure 15:
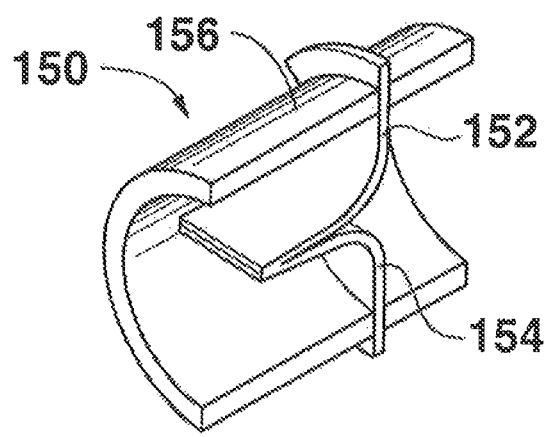
FIG. 15 is a perspective view with cut away portions of the check valve illustrated in FIG. 14.

The second valve device 100 as shown in FIG. 5 represents one embodiment of a check valve (a valve that allows flow in one direction) that may be used in accordance with the present disclosure. It should be understood, however, that various other check valves may be used. For instance, referring to FIGS. 14 through 18, another embodiment of a check valve device 150 is illustrated. As shown in FIGS. 14 and 15, for instance, the check valve device 150 includes a pair of overlapping flaps 152 and 154. The overlapping flaps allow fluid flow only in one direction. As shown, the opposing flaps 152 and 154 are generally planar and parallel. The flaps can be integral with the arteriovenous graft 156 or can be attached to the graft using any suitable technique. For instance, as shown in FIG. 15, the arteriovenous graft 156 can include a pair of opposing slits through which the flaps are inserted. The flaps can then be attached to the graft 156 by being welded in place or through the use of a biocompatible adhesive. In an alternative embodiment as shown in FIG. 18, sutures 158 can be used in order to attach the flaps o the arteriovenous graft 156.

Figure 16:
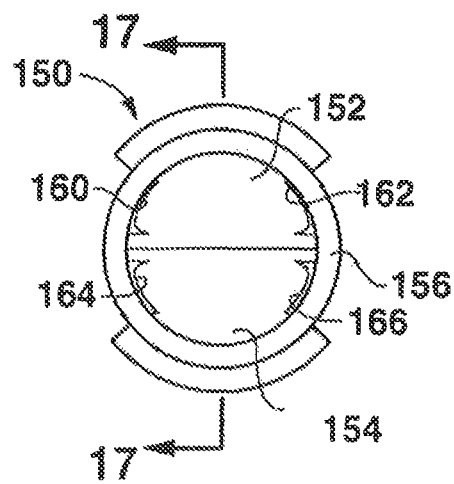
FIG. 16 is a cross-sectional view of the check valve illustrated in FIG. 14.
Figure 17:
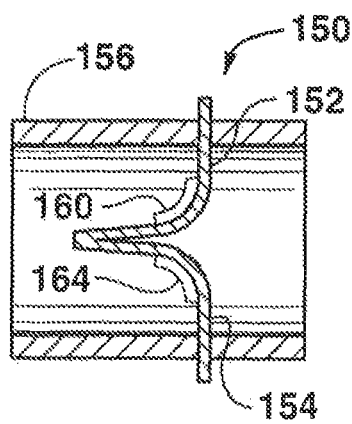
FIG. 17 is a cross-sectional view taken along line A-A of the check valve illustrated in FIG. 16.
Figure 18:
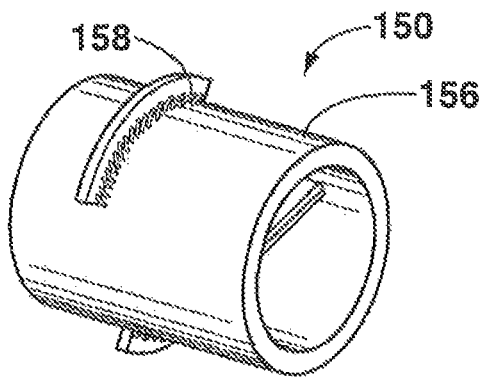
FIG. 18 is an alternative embodiment of a check valve that may be used in accordance with the present disclosure.

In addition to the flaps 152 and 154, the check valve device 150 can further include edge seals 160, 162, 164 and 166 as shown in FIGS. 16 and 17. The edge seals 160, 162, 164 and 166 are positioned on both sides of each flap and are designed to create a seal with the radial wall of the graft 156. The edge seals are generally located where the flaps are not connected to the graft 156, The check valve device 150 can be made from any suitable material. For instance, the flaps and the edge seals can be made from expanded or unexpanded PTFE, polyurethane and/or silicone. The blood contacting surfaces may be treated and/or textured to enhance their formation of a pseudointima, optimize thrombocompatibility and flow characteristics.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An arteriovenous graft system comprising:
an arteriovenous graft having an arterial end and an opposite venous end;
a valve device associated with the arteriovenous graft, the valve device including an inflatable balloon having a deflated state and an inflated state; and
a magnetically activated actuator in fluid communication with the inflatable balloon, the magnetically activated actuator being configured to actuate the inflatable balloon between the inflated state and the deflated state by controlling a flow of fluid between the magnetically activated actuator and the inflatable balloon.

2. The arteriovenous graft system of claim 1, wherein, when a magnetic force is applied to the magnetically activated actuator, the fluid is directed between the magnetically activated actuator and the inflatable balloon.

3. The arteriovenous graft system of claim 2, wherein, when the magnetic force is applied to the magnetically activated actuator, the fluid is drawn out of the inflatable balloon so as to cause the inflatable balloon to be actuated to its deflated state.

4. The arteriovenous graft system of claim 1, further comprising an external magnetic key, the external magnetic key being configured to apply a magnetic force to the magnetically activated actuator so as to cause the fluid to be directed between the magnetically activated actuator and the inflatable balloon.

5. The arteriovenous graft system of claim 4, wherein the external magnetic key is configured to be positioned adjacent to a patient's skin so as to apply the magnetic force to the magnetically activated actuator.

6. The arteriovenous graft system of claim 5, wherein, when the external magnetic key is placed adjacent to the patient's skin, the magnetic force applied to the magnetically activated actuator causes the inflatable balloon to be actuated to its deflated state.

7. The s arteriovenous graft system of claim 1, wherein the magnetically activated actuator comprises a magnetically activated piston disposed within a subcutaneously implanted housing.

8. The arteriovenous graft system of claim 1, further comprising a fluid conduit coupled between the magnetically activated actuator and the valve device, the flow of fluid being directed through the fluid conduit.

9. The arteriovenous graft system of claim 1, wherein, when the inflatable balloon is in the deflated state, the valve device is open to allow a flow of blood through the arteriovenous graft.

10. The arteriovenous graft system of claim 1, wherein, when the inflatable balloon is in the inflated state, the valve device is closed to prevent a flow of blood through the arteriovenous graft.

11. The arteriovenous graft system of claim 1, wherein the valve device is located at the arterial end or the venous end of the arteriovenous graft.

12. An arteriovenous graft system comprising:
an arteriovenous graft having an arterial end and an opposite venous end;
a valve device associated with the arteriovenous graft, the valve device including an inflatable balloon having a deflated state and an inflated state; and
a magnetically activated actuator in fluid communication with the inflatable balloon, the magnetically activated actuator being configured to actuate the inflatable balloon between the inflated state and the deflated state by controlling a flow of fluid between the magnetically activated actuator and the inflatable balloon; and
an external magnetic key, the external magnetic key being configured to apply a magnetic force to the magnetically activated actuator so as to cause the fluid to be directed between the magnetically activated actuator and the inflatable balloon.

13. The arteriovenous graft system of claim 12, wherein, when the magnetic force is applied to the magnetically activated actuator, the fluid is drawn out of the inflatable balloon so as to cause the inflatable balloon to be actuated to its deflated state.

14. The arteriovenous graft system of claim 12, wherein the external magnetic key is configured to be positioned adjacent to a patient's skin so as to apply the magnetic force to the magnetically activated actuator.

15. The arteriovenous graft system of claim 14, wherein, when the external magnetic key is placed adjacent to the patient's skin, the magnetic force applied to the magnetically activated actuator causes the inflatable balloon to be actuated to its deflated state.

16. The arteriovenous graft system of claim 12, wherein the magnetically activated actuator comprises a magnetically activated piston disposed within a subcutaneously implanted housing.

17. The arteriovenous graft system of claim 12, further comprising a fluid conduit coupled between the magnetically activated actuator and the valve device, the flow of fluid being directed through the fluid conduit.

18. The arteriovenous graft system of claim 12, wherein, when the inflatable balloon is in the deflated state, the valve device is open to allow a flow of blood through the arteriovenous graft and wherein, when the inflatable balloon is in the inflated state, the valve device is closed to prevent the flow of blood through the arteriovenous graft.

19. The arteriovenous graft system of claim 12, wherein the valve device is located at the arterial end or the venous end of the arteriovenous graft.

20. A hemodialysis method comprising:
subcutaneously implanting an arteriovenous graft system in a patient, the arteriovenous graft system including an arteriovenous graft having a valve device associated therewith, the valve device including an inflatable balloon having a deflated state and an inflated state, the arteriovenous graft system further including a magnetically activated actuator in fluid communication with the inflatable balloon, the magnetically activated actuator being configured to actuate the inflatable balloon between the inflated state and the deflated state by controlling a flow of fluid between the magnetically activated actuator and the inflatable balloon; and
applying a magnetic force to the magnetically activated actuator such that the fluid is directed between the magnetically activated actuator and the inflatable balloon.

* * * * *